United States Patent
Matula, Jr. et al.

(10) Patent No.: US 9,604,023 B2
(45) Date of Patent: Mar. 28, 2017

(54) RESPIRATORY MASK WITH RIBBED CONTACTING SURFACE

(75) Inventors: Jerome Matula, Jr., Apollo, PA (US); Derrick Blake Andrews, Markleton, PA (US); Peter Chi Fai Ho, Pittsburgh, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 886 days.

(21) Appl. No.: 13/638,020

(22) PCT Filed: Mar. 28, 2011

(86) PCT No.: PCT/IB2011/051309
§ 371 (c)(1),
(2), (4) Date: Sep. 28, 2012

(87) PCT Pub. No.: WO2011/121525
PCT Pub. Date: Oct. 6, 2011

(65) Prior Publication Data
US 2013/0014760 A1    Jan. 17, 2013

Related U.S. Application Data

(60) Provisional application No. 61/319,399, filed on Mar. 31, 2010.

(51) Int. Cl.
*A61M 16/06* (2006.01)
(52) U.S. Cl.
CPC ........ *A61M 16/06* (2013.01); *A61M 16/0616* (2014.02); *A61M 16/0633* (2014.02); *A61M 16/0683* (2013.01); *A61M 2205/42* (2013.01)

(58) Field of Classification Search
CPC .. A61M 16/00; A61M 16/06; A61M 16/0605; A61M 16/0616; A61M 16/0627; A61M 2210/0606; A61M 2210/0618; A61M 2210/0625
See application file for complete search history.

(56) References Cited

U.S. PATENT DOCUMENTS

| | | | | |
|---|---|---|---|---|
| 1,653,572 A | * | 12/1927 | Jackson | 128/206.24 |
| 2,939,458 A | * | 6/1960 | Lundquist | 128/206.25 |
| 7,007,696 B2 | * | 3/2006 | Palkon et al. | 128/207.13 |
| 7,243,651 B2 | | 7/2007 | Kwok | |

(Continued)

FOREIGN PATENT DOCUMENTS

| | | |
|---|---|---|
| CN | 101155618 A | 4/2008 |
| DE | 202008012074 U1 | 1/2009 |

(Continued)

*Primary Examiner* — Justine Yu
*Assistant Examiner* — Michael Tsai
(74) *Attorney, Agent, or Firm* — Michael W. Haas

(57) ABSTRACT

A patient interface device (8) for delivering a flow of breathing gas to an airway of a patient is provided that includes a patient contacting component (9, 90) having a patient contacting surface structured to engage the face of the patient when the patient interface device is donned by the patient, the patient contacting surface also including a plurality of ribs (40, 52, 62, 72, 82, 96) extending therefrom. The patient contacting component may be, without limitation, a mask having a mask cushion, a forehead support having a forehead cushion, a cheek pad or a chin pad.

12 Claims, 11 Drawing Sheets

(56) References Cited

U.S. PATENT DOCUMENTS

| | | |
|---|---|---|
| 7,287,528 B2 | 10/2007 | Ho |
| 8,267,089 B2 | 9/2012 | Ho |
| 8,807,135 B2 * | 8/2014 | Worboys et al. ........ 128/206.24 |
| 2005/0022818 A1 | 2/2005 | Kwok |
| 2008/0257354 A1 * | 10/2008 | Davidson et al. ....... 128/206.24 |
| 2009/0014007 A1 | 1/2009 | Brambilla |
| 2010/0059058 A1 | 3/2010 | Kuo |

FOREIGN PATENT DOCUMENTS

| | | |
|---|---|---|
| EP | 1334742 A2 | 8/2003 |
| GB | 428338 A | 5/1935 |
| GB | 447729 A | 5/1936 |
| JP | 2502161 B2 | 5/1996 |
| JP | 2939458 B2 | 8/1999 |
| WO | WO2009108995 A1 | 9/2009 |

* cited by examiner

RESPIRATORY MASK WITH RIBBED CONTACTING SURFACE

CROSS-REFERENCE TO RELATED APPLICATIONS

This patent application claims the priority benefit under 35 U.S.C. §371 of international patent application no. PCT/IB2011/050784, filed Feb. 24, 2011, which claims the priority benefit under 35 U.S.C. §119(e) of U.S. Provisional Application No. 61/317,429 filed on Mar. 25, 2010, the contents of which are herein incorporated by reference.

This patent application claims the priority benefit under 35 U.S.C. §119(e) of U.S. Provisional Application No. 61/319,399 filed on Mar. 31, 2010, the contents of which are herein incorporated by reference.

BACKGROUND OF THE INVENTION

1. Field of the Disclosure

The present invention relates to patient interface devices for transporting a gas to and/or from an airway of a user, and, in particular, to a patient interface device including a patient contacting component, such as a mask having a mask cushion, that has a ribbed patient contacting surface.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver positive airway pressure (PAP) therapy to treat certain medical disorders, the most notable of which is obstructive sleep apnea (OSA). Known PAP therapies include continuous positive airway pressure (CPAP), wherein a constant positive pressure is provided to the airway of the patient in order to splint open the patient's airway, and variable airway pressure, wherein the pressure provided to the airway of the patient is varied with the patient's respiratory cycle. Such therapies are typically provided to the patient at night while the patient is sleeping.

Non-invasive ventilation and pressure support therapies as just described involve the placement of a patient interface device including a mask component having a soft, flexible cushion on the face of a patient. The mask component may be, without limitation, a nasal mask that covers the patient's nose, a nasal cushion having nasal prongs that are received within the patient's nares, a nasal/oral mask that covers the nose and mouth, or a full face mask that covers the patient's face. Such patient interface device may also employ other patient contacting components, such as forehead supports, cheek pads and chin pads. The patient interface device interfaces the ventilator or pressure support device with the airway of the patient, so that a flow of breathing gas can be delivered from the pressure/flow generating device to the airway of the patient. It is known to maintain such devices on the face of a wearer by a headgear having one or more straps adapted to fit over/around the patient's head.

Current mask cushions are of a singular, thin curved flap design that contacts the skin surface of the patient. The single flap, combined with a wide thin surface area, contribute to the formation of channels which allow air to escape. This makes it very difficult to achieve a positive seal on a wide variety of patient faces. Additionally, the escaping air sometimes induces unwanted vibrations in the cushion which often results in loud, unpleasant noises similar to flatulence. Similar problems may also presented by other patient contacting components of patient interface devices.

SUMMARY OF THE INVENTION

Accordingly, it is an object of the present invention to provide a patient interface device that overcomes the shortcomings of conventional such device. This object is achieved according to one embodiment of the present invention by providing a patient interface device for delivering a flow of breathing gas to an airway of a patient that includes a patient contacting component having a flexible patient contacting surface structured to engage a face of the patient when the patient interface device is donned by the patient. The patient contacting surface also includes a plurality of flexible ribs extending therefrom. The patient contacting component may be, without limitation, a mask having a mask cushion, a forehead support having a forehead cushion, a cheek pad or a chin pad.

In another embodiment, a pressure support system is provided that includes a pressure generating device structured to produce a flow of breathing gas, and a patient interface device operatively coupled to the pressure generating system and structured to deliver the flow of breathing gas to an airway of a patient. The patient interface device includes a patient contacting component having a flexible patient contacting surface structured to engage a face of the patient when the patient interface device is donned by the patient, the patient contacting surface including a plurality of flexible ribs extending therefrom.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
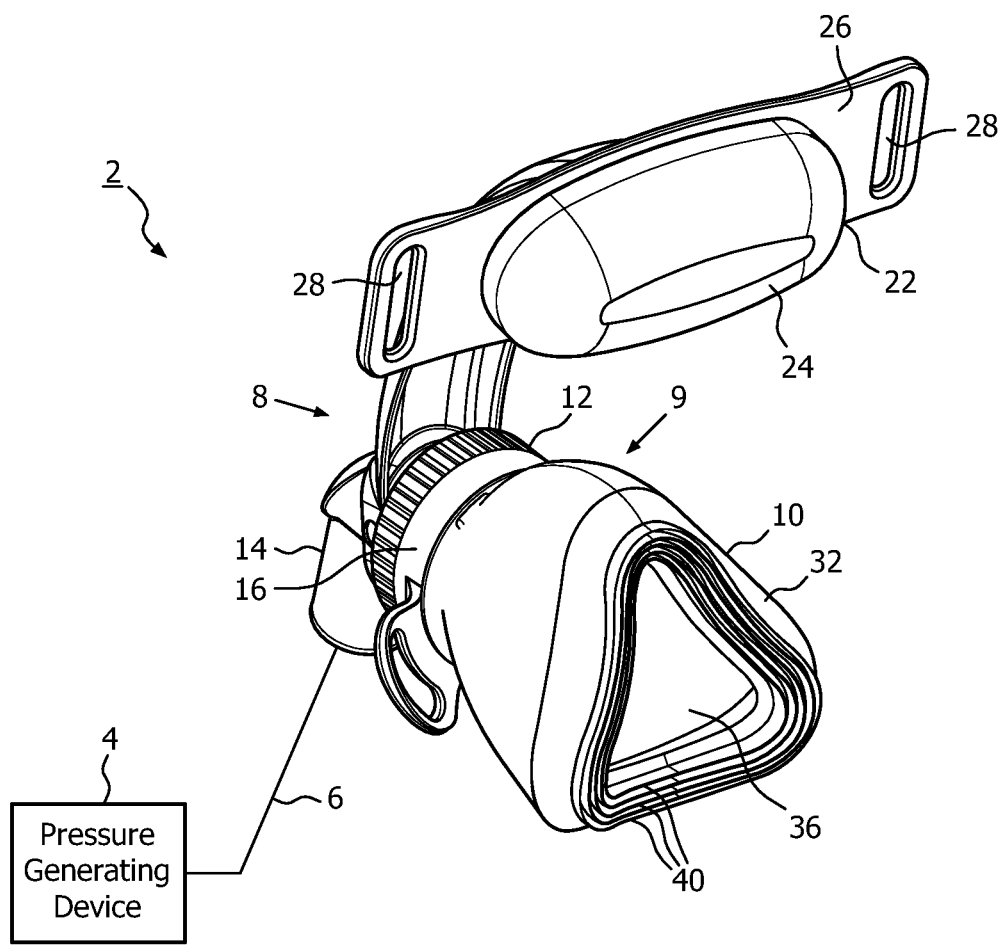
FIG. 1 is an isometric view.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 2:
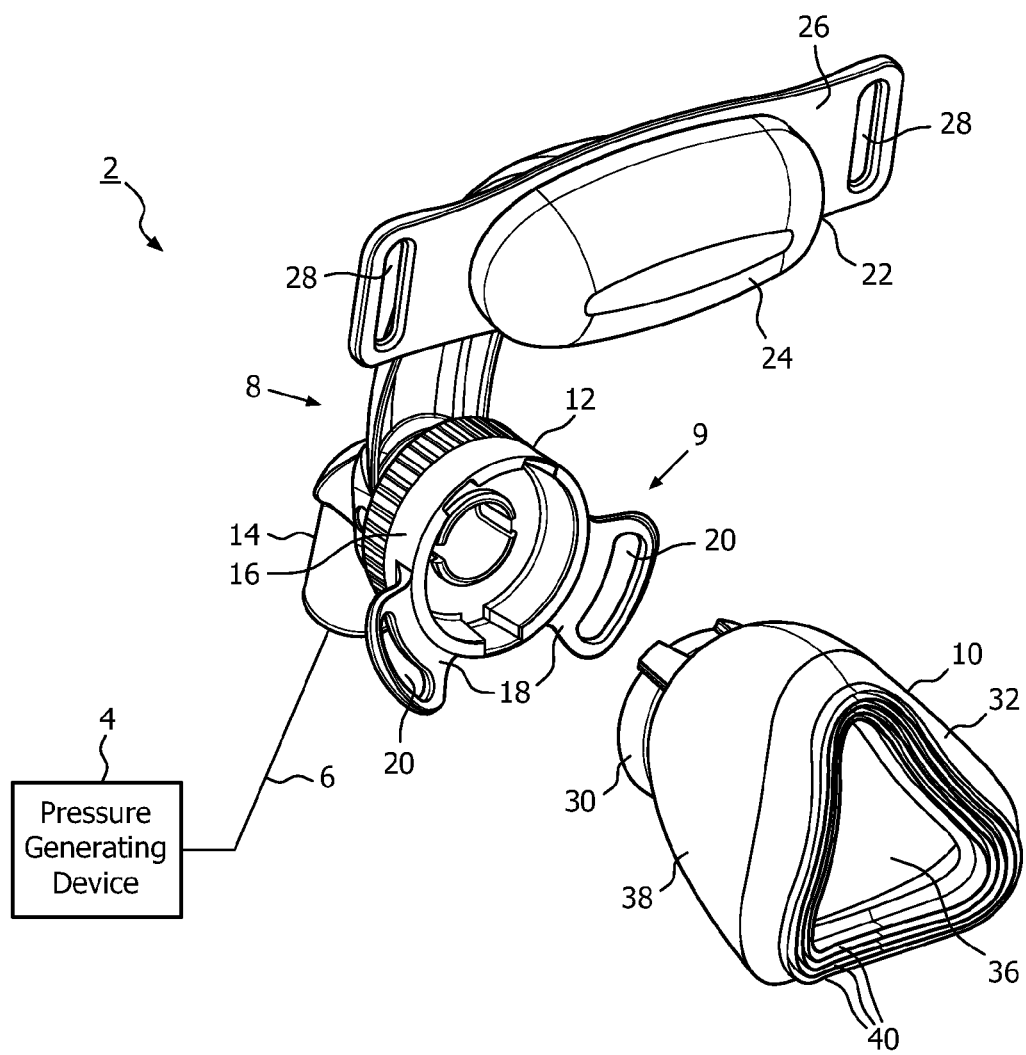
FIG. 2 is a partially exploded view of a system adapted to provide a regimen of respiratory therapy to a patient according to one exemplary embodiment of the present invention.
Figure 3:
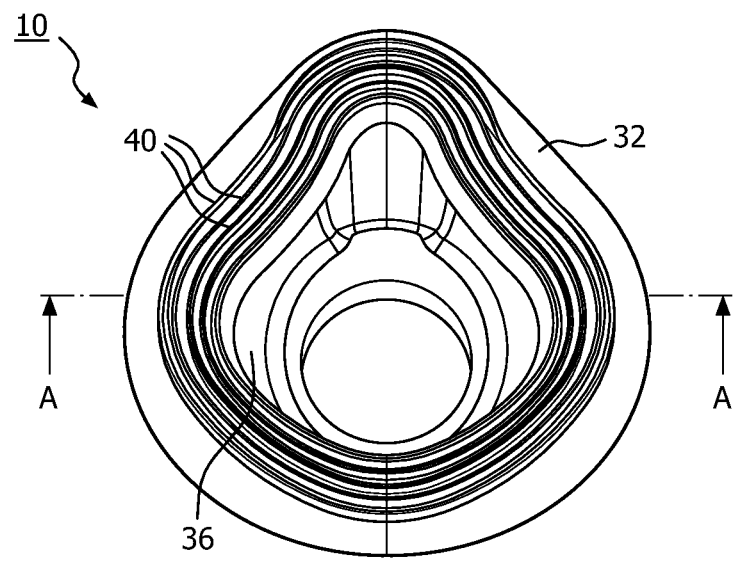
FIG. 3 is a front elevational view of the sealing cushion forming a part of the mask of the system of FIGS. 1 and 2.

FIG. 1 is an isometric view and FIG. 2 is a partially exploded view of a system 2 adapted to provide a regimen of respiratory therapy to a patient according to one exemplary embodiment of the present invention. System 2 provides a regimen of respiratory therapy to a patient according to one embodiment is generally shown in FIGS. 1-3. System 2 includes a pressure generating device 4, a delivery conduit 6, and a patient interface device 8 (delivery conduit 6 and patient interface device 8 are together often referred to as a patient circuit). Pressure generating device 4 is structured to generate a flow of breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, Pa.), and auto-titration pressure support devices. Delivery conduit 6 is structured to communicate the flow of breathing gas from pressure generating device 4 to patient interface device 8.

Patient interface device 8 includes a mask 9, which in the illustrated embodiment is a nasal mask. However, any type of mask, such as a nasal/oral mask, a nasal cushion or a full face mask, which facilitates the delivery of a flow of breathing gas to the airway of a patient, may be used as mask 9 while remaining within the scope of the present invention. Mask 9 includes a sealing cushion 10, which is fluidly coupled to a rigid support structure 12. In the illustrated embodiment, sealing cushion 10 is defined from a unitary piece of soft, flexible, cushiony, elastomeric material, such as, without limitation, silicone, an appropriately soft thermoplastic elastomer, a gel, a closed cell foam, or any combination of such materials. Support structure 12 is fluidly coupled to an elbow conduit 14. Elbow conduit 14 is structured to be coupled to delivery conduit 6 which is in fluid communication with pressure generating device 4.

Support structure 12 includes a base portion 16 having a pair of extension members 18 extending from opposites side thereof, wherein each extension member 18 includes a loop 20, which is structured to receive a respective lower headgear strap of a headgear assembly (not shown) for securing patient interface device 8 to the head of the patient. Patient interface device 8 further includes a forehead support 22 that includes a forehead cushion 24 coupled to a support frame 26. Forehead support 22 is structured to provide additional support for patient interface device 8 by engaging the forehead of the patient. Support frame 26 includes loops 28 provided at opposite ends thereof. Each loop 28 is structured to receive a respective upper headgear strap of a headgear assembly (not shown) for securing patient interface device 8 to the head of the patient.

Figure 4:
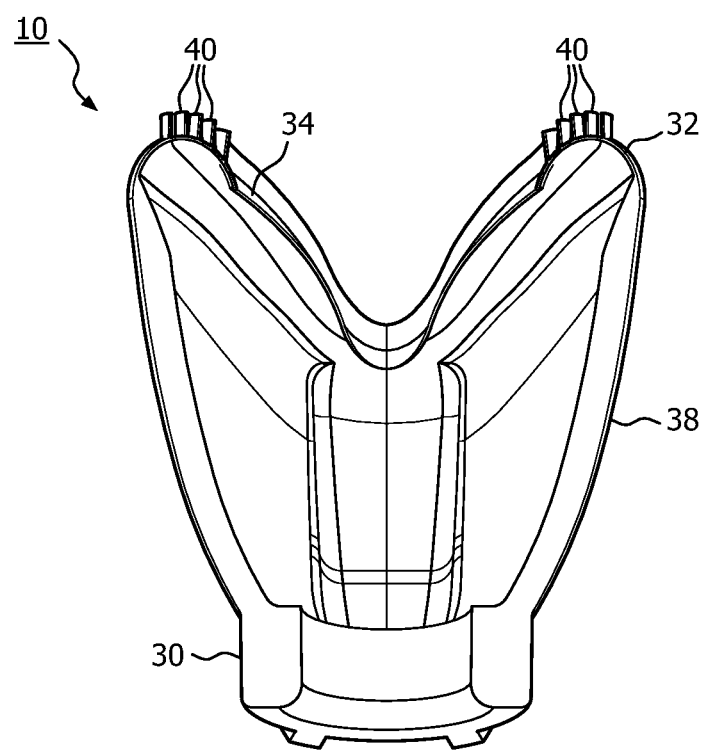
FIG. 4 is a cross-sectional view of the sealing cushion shown in FIG. 3 taken along lines A-A of FIG. 3.

FIG. 3 is a front elevational view of sealing cushion 10, and FIG. 4 is a cross-sectional view of sealing cushion 10 taken along lines A-A of FIG. 3. Sealing cushion 10 includes a first end portion 30 that couples to support structure 12. In the illustrated embodiment, first end portion 30 is generally cylindrically shaped and attaches to a similarly-shaped opening provided in base portion 16 of support structure 12. It is to be further understood that the present invention contemplates using any conventional technique for attaching the first end portion of the seal to the mask shell. Such techniques include permanently bonding the seal to the mask shell, for example, using adhesives, mechanical fasteners, or molding the seal onto the shell such that the seal is selectively detachable from the mask shell.

Sealing cushion 10 includes a second end portion 32 for sealing engagement with a face of a patient. Second end portion 32 includes a first in-turned flap 34 which is generally turned into a nose receiving cavity 36. A sidewall 38 extends between first end portion 30 and second end portion 32.

When coupled to support structure 12, sealing cushion 10 defines a chamber for receiving a portion of the patient when the mask is donned by the patient. Typically, a portion of the patient, such as the patient's nose ion the illustrated embodiment, inserts into the chamber so that the patient's airway is in fluid communication with the chamber.

According to the principles of the present invention, a portion of the exposed surface of second end portion 32 includes a plurality of ribs 40 extending therefrom. In the embodiment of FIGS. 1-4, each rib 40 has an identical height and thickness, and the spacing between each adjacent pair of ribs 40 is identical. As will be appreciated, the magnitude of the height, thickness, and spacing in any particular application will be dictated by the circumstances and requirements of the application. In addition, each rib 40 extends concentrically and continuously along the exposed surface of second end portion 32 around the opening defining nose receiving cavity 36. In one embodiment, each rib 40 is made of the same material (e.g., the same material as the remainder of sealing cushion 10). In another embodiment, individual ribs may be made of varying materials, such as those described elsewhere herein.

Sealing cushion 10 having ribs 40 as just described is advantageous because the multiple ribs act as a series of individual flaps which individually provide a seal against the face of the patient. If one of the ribs 40 develops a leak, the other ribs 40 can seal against the leak. Therefore, even if many individual leaks are present, sealing cushion 10 will still as a whole provide a leak-proof seal against the face of the patient. In addition, as described elsewhere herein, prior art cushions which employ a large, thin surface that contacts the patient's skin often result in significant vibration and/or noise during use. The presence of multiple ribs 40 in the present invention helps to reduce or eliminate such vibrations and noise. The multiple ribs at the sealing surface of the cushion also provide increased comfort for the patient as they will readily conform to the shape of the patient's face anatomy and provide a soft, feathery texture.

Figure 5:
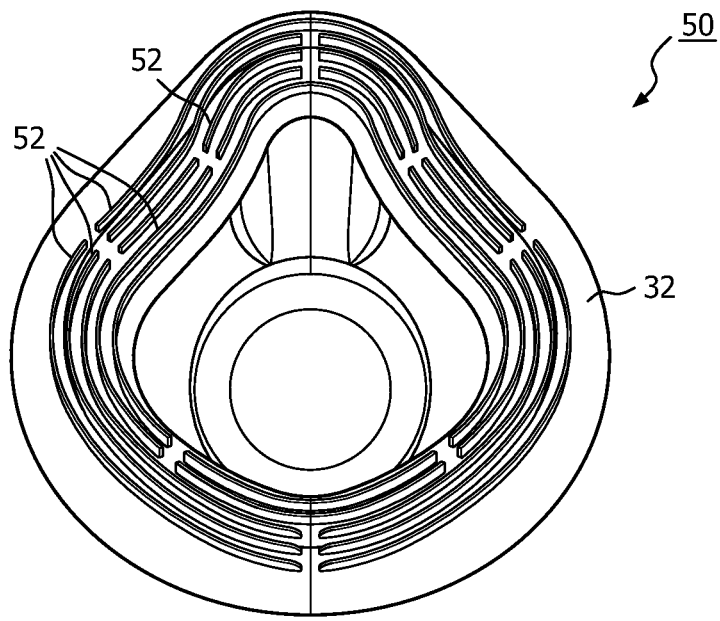
FIG. 5 is a front elevational view.
Figure 6:
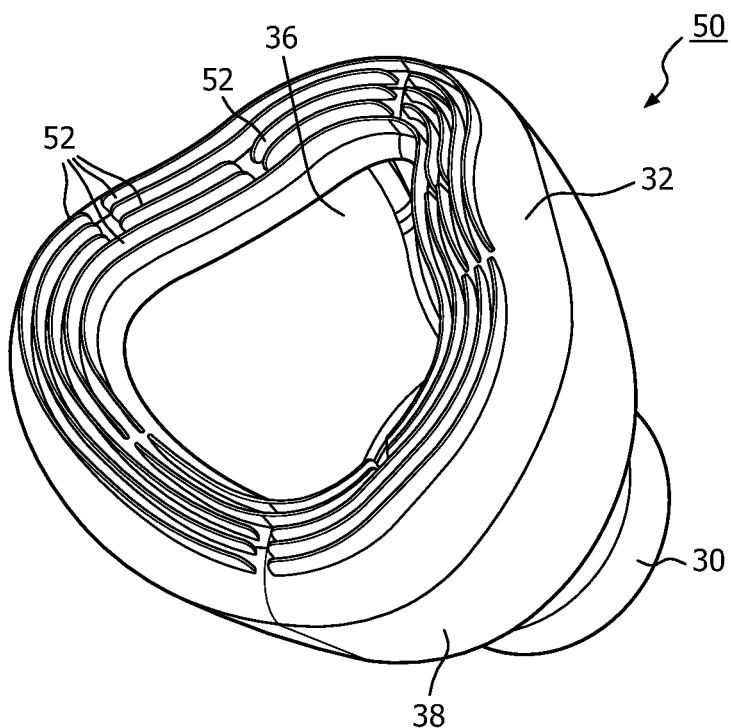
FIG. 6 is an isometric view of a sealing cushion according to an alternative exemplary embodiment of the invention that may be used in the mask of the system of FIGS. 1 and 2.

FIG. 5 is a front elevational view and FIG. 6 is an isometric view of sealing cushion 50 according to an alternative exemplary embodiment of the invention. Sealing cushion 50 may be substituted for sealing cushion 10 in patient interface device 8. Sealing cushion 50 includes a plurality of ribs 52 extending from the exposed surface of second end portion 32. Unlike ribs 40 of sealing cushion 10, ribs 52 do not extend continuously along the exposed surface of second end portion 32 around the opening defining nose receiving cavity 36. Instead, ribs 52 having varying lengths so as to form an intermittent, concentric pattern on the exposed surface of second end portion 32. In the illustrated embodiment, each rib 52 has an identical height and thickness, and the spacing between each adjacent pair of ribs 52 is identical.

Figure 7:
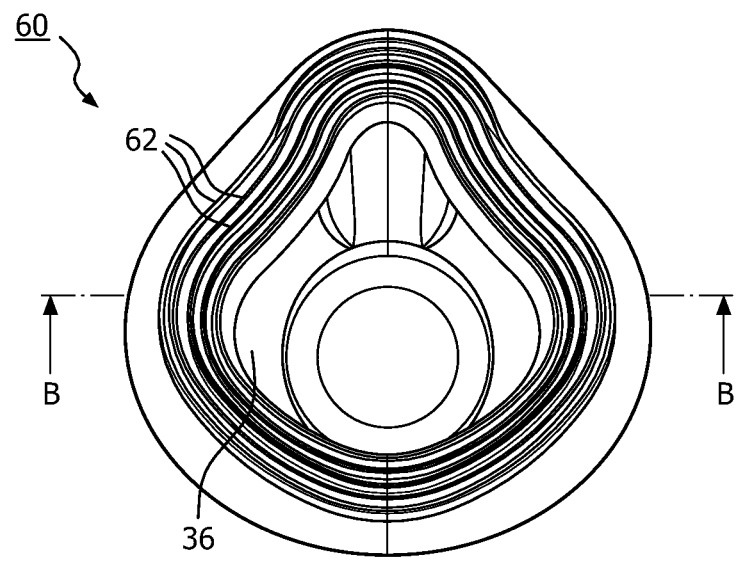
FIG. 7 is a front elevational view.
Figure 8:
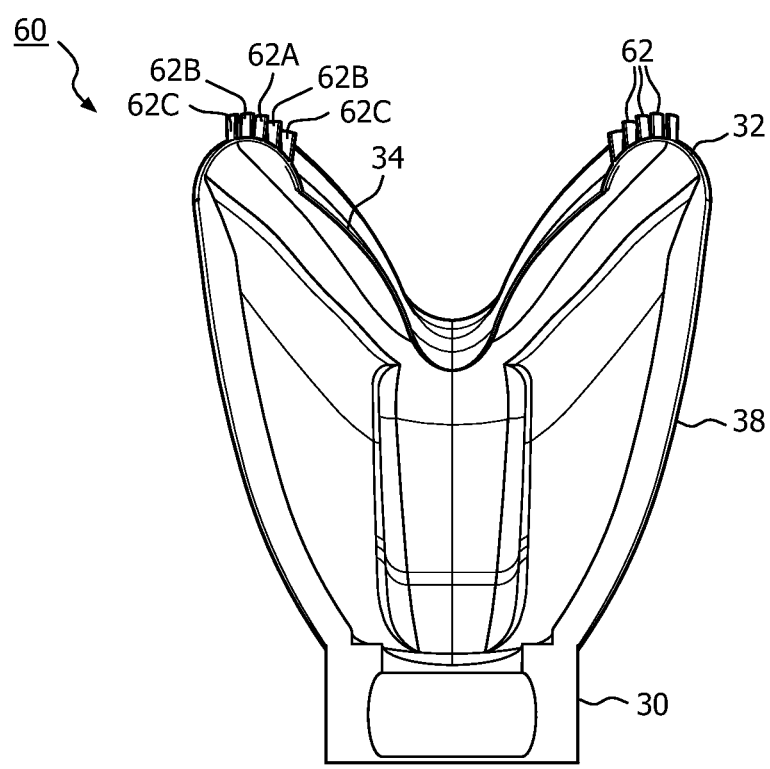
FIG. 8 is a cross-sectional view of taken along lines B-B of FIG. 7.
Figure 9:
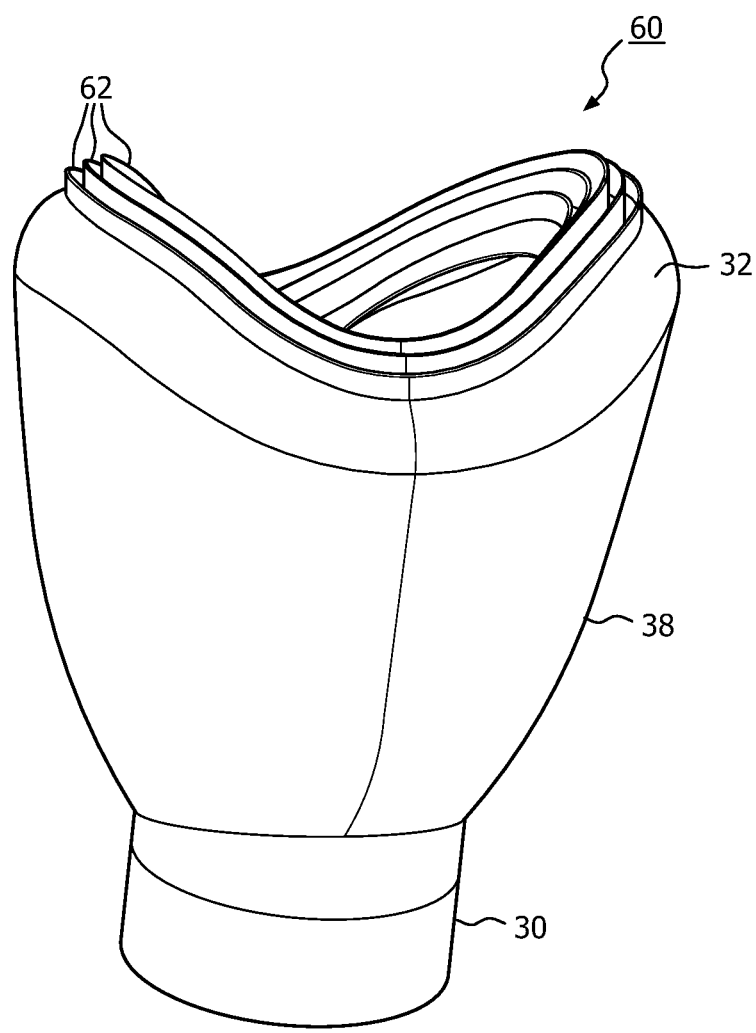
FIG. 9 is a side isometric view of a sealing cushion according to a further alternative exemplary embodiment of the invention that may be used in the mask of the system of FIGS. 1 and 2.

FIG. 7 is a front elevational view, FIG. 8 is a cross-sectional view of taken along lines B-B of FIG. 7, and FIG. 9 is a side isometric view of a sealing cushion 60 according to a further alternative exemplary embodiment of the invention. Sealing cushion 60 may be substituted for sealing cushion 10 in patient interface device 8. Sealing cushion 60 includes a plurality of ribs 62 extending from the exposed surface of second end portion 32. As seen in FIGS. 7-9, each rib 62 has an identical thickness, and the spacing between each adjacent pair of ribs 62 is identical. In addition, each of the ribs 62 extends continuously along the exposed surface of second end portion 32 around the opening defining nose receiving cavity 36. However, unlike ribs 40 and 52, the height of ribs 62 varies. In the illustrated embodiment, ribs 62 comprise a central rib 62A having the greatest height, a pair of middle ribs 62B having the next greatest height, and a pair of outside ribs 62C having the smallest height (FIG. 8). As will be appreciated, the magnitude of the different heights in any particular application will be dictated by the circumstances and requirements of the application.

Figure 10:
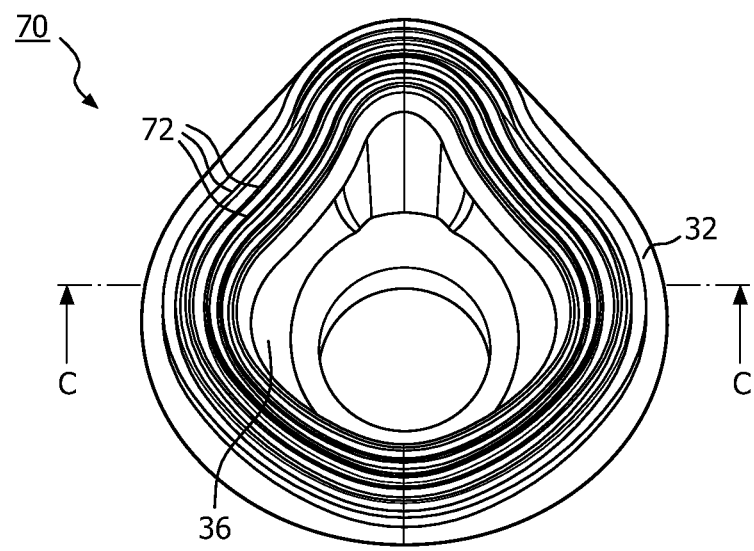
FIG. 10 is a front elevational view.
Figure 11:
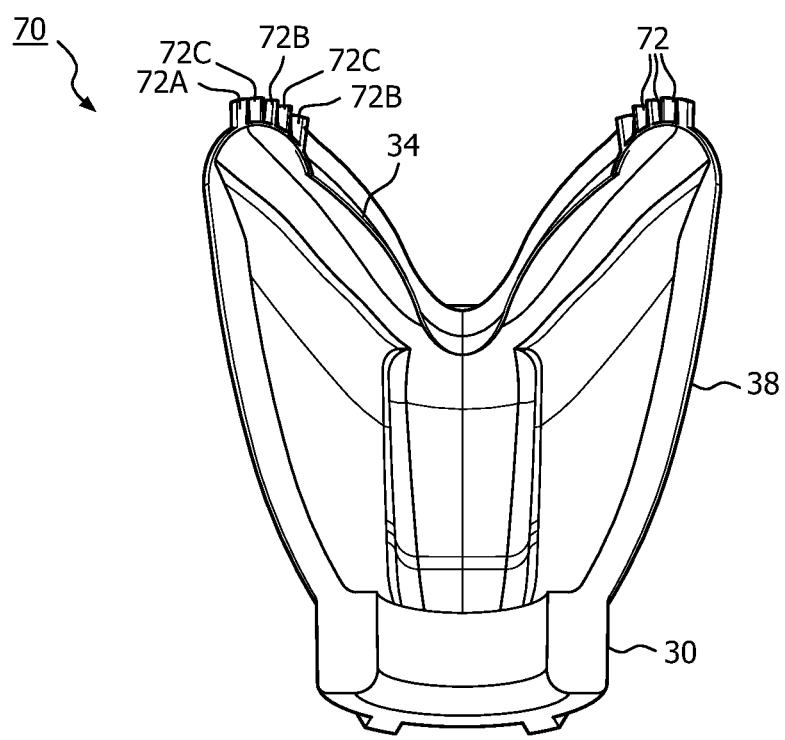
FIG. 11 is a cross-sectional view of taken along lines C-C of FIG. 10.
Figure 12:
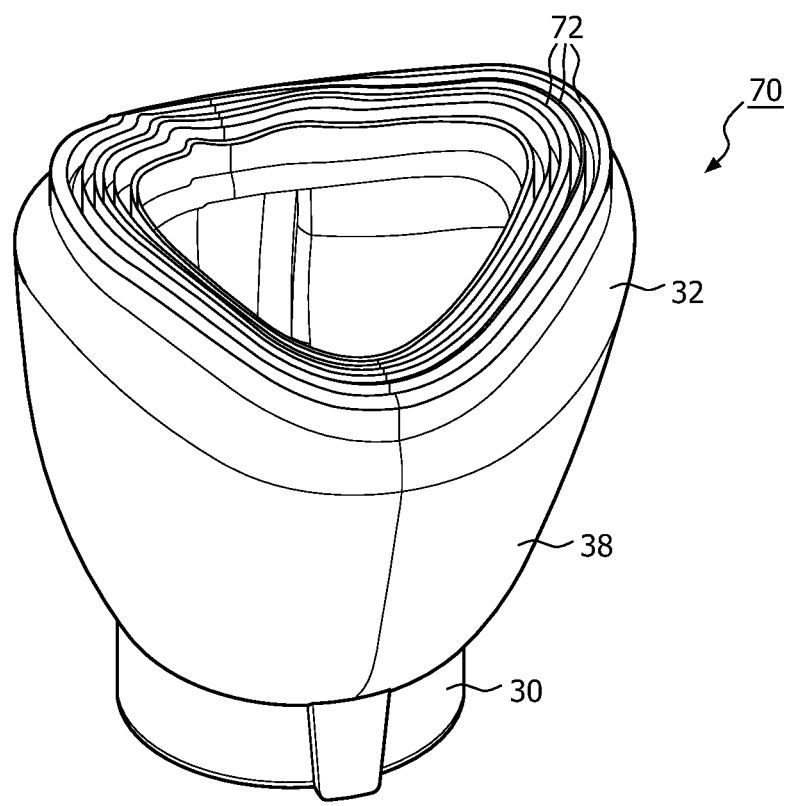
FIG. 12 is a side isometric view of a sealing cushion according to another alternative exemplary embodiment of the invention that may be used in the mask of the system of FIGS. 1 and 2.

FIG. 10 is a front elevational view, FIG. 11 is a cross-sectional view of taken along lines C-C of FIG. 10, and FIG. 12 is a side isometric view of a sealing cushion 70 according to another alternative exemplary embodiment of the invention. Sealing cushion 70 may be substituted for sealing cushion 10 in patient interface device 8. Sealing cushion 70 includes a plurality of ribs 72 extending from the exposed surface of second end portion 32. As seen in FIGS. 10-12, each rib 72 has an identical height, and the spacing between each adjacent pair of ribs 72 is identical. In addition, each of the ribs 72 extends continuously along the exposed surface of second end portion 32 around the opening defining nose receiving cavity 36. However, unlike ribs 40, 52 and 62, the thickness of ribs 62 varies. In the illustrated embodiment, ribs 62 comprise a first rib 72A having the greatest thickness, a pair of second ribs 72B having the next greatest thickness, and a pair of third ribs 72C having the smallest thickness (FIG. 11). As will be appreciated, the magnitude of the different thicknesses in any particular application will be dictated by the circumstances and requirements of the application.

Figure 13:
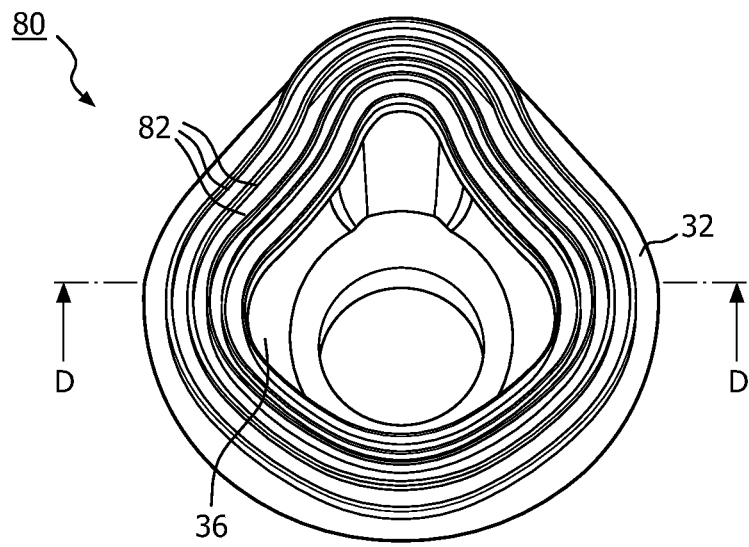
FIG. 13 is a front elevational view.
Figure 14:
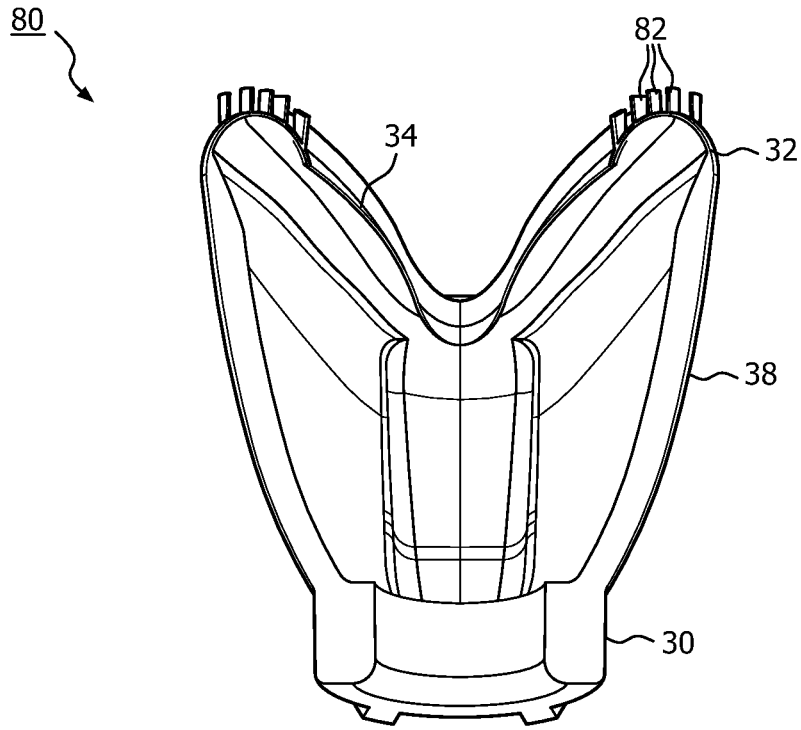
FIG. 14 is a cross-sectional view of taken along lines D-D of FIG. 13.
Figure 15:
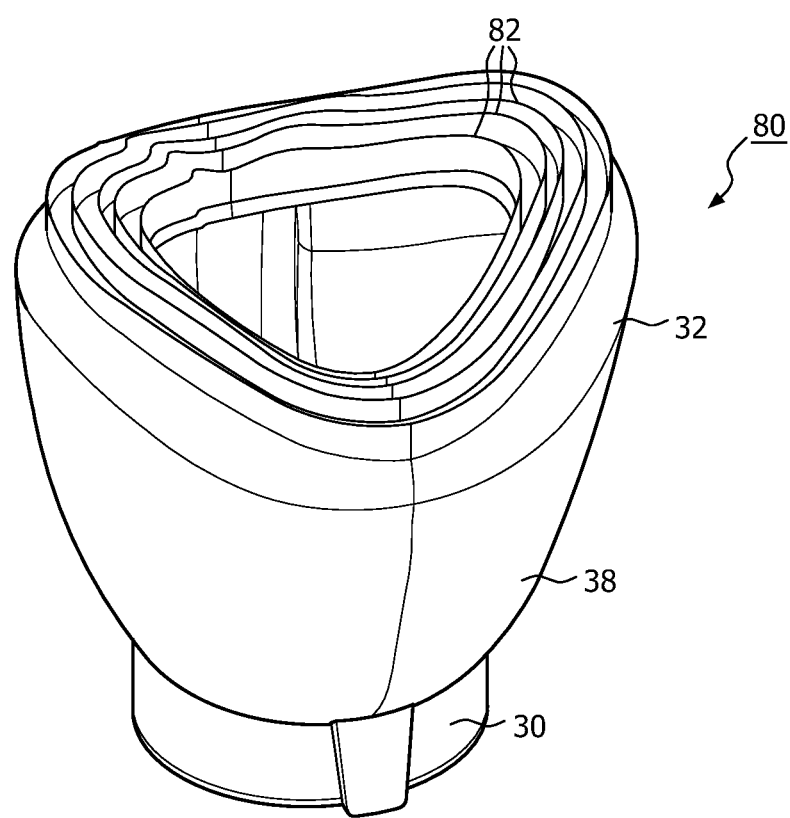
FIG. 15 is a side isometric view of a sealing cushion according to yet another alternative exemplary embodiment of the invention that may be used in the mask of the system of FIGS. 1 and 2.

FIG. 13 is a front elevational view, FIG. 14 is a cross-sectional view of taken along lines D-D of FIG. 13, and FIG. 15 is a side isometric view of sealing cushion 80 according to still another alternative exemplary embodiment of the invention. Sealing cushion 80 may be substituted for sealing cushion 10 in patient interface device 8. Sealing cushion 80 includes a plurality of ribs 82 extending from the exposed surface of second end portion 32. As seen in FIGS. 13-15, each of ribs 82 has an identical height and thickness. In addition, each of the ribs 82 extends continuously along the exposed surface of second end portion 32 around the opening defining nose receiving cavity 36. However, unlike ribs 40, 52, 62, and 72, the spacing between each adjacent pair of ribs 72 varies. As will be appreciated, the magnitude of the different spacings in any particular application will be dictated by the circumstances and requirements of the application.

In the embodiments discussed above, the height of each rib (distance from peak to trough) is 0.5-3.0 mm, and, in one embodiment, the ribs are formed using a molding process, such as being molded along with the molding of the cushion. The present invention also contemplates, however, that the ribs can have a much shorter height, such as 25-200 microns (0.025-0.200 mm). Also, the spacing between the ribs can be smaller, such as 25-150 microns (0.025-0.150 mm). That is the distance from peak (crest) to peak (crest) can be 0.15 mm. In an exemplary embodiment, forming ribs of this small size can be accomplished using nano etching.

By using such small scale ribs, a much greater number of ribs can be provided around the perimeter of the cushion, thus increasing the sealing ability of the ribs while maintaining comfort for the patient. Also, using this type of etching allows the ribs to be providing on a wide variety of surfaces, includes surfaces with contours that is difficult to do using conventional molding techniques.

Figure 16:
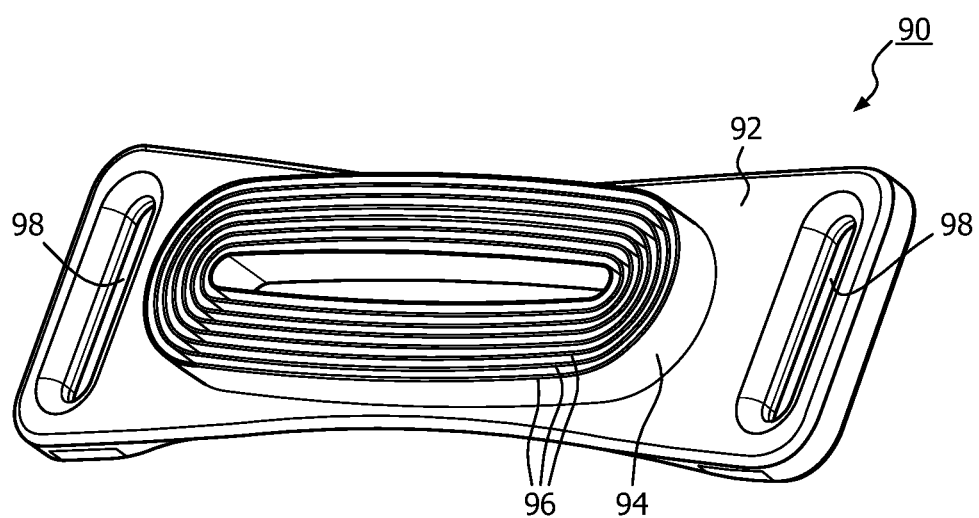
FIG. 16 is an isometric view of a forehead support according to an alternative embodiment of the invention.

FIG. 16 is an isometric view of a forehead support 90 according to an alternative embodiment of the invention. Forehead support 90 is structured to provide additional support for a patient interface device by engaging the forehead of the patient, and may be substituted for forehead support 22 of patient interface device 8 described elsewhere herein. Forehead support 90 includes a forehead cushion 94 that is coupled to support frame 92. Forehead cushion 94 is made from a soft, flexible, cushiony, elastomeric material, such as, without limitation, silicone, an appropriately soft thermoplastic elastomer, a closed cell foam, or any combination of such materials. Support frame 92 includes loops 98 provided at opposite ends thereof. Each loop 98 is structured to receive a respective upper headgear strap of a headgear assembly (not shown) for securing the associated patient interface device to the head of the patient. Forehead cushion 94 includes a plurality of continuous, oblong ribs 96 extending outwardly from support frame 92. The number, size, shape, configuration, and spacing between ribs 96 is meant to be exemplary only, and it should be understood that other rib numbers, sizes, shapes, configurations and spacing, such as, without limitation, those described elsewhere herein, may also be employed.

In addition, the invention as described herein is not limited to use with just mask and forehead cushions. Rather, ribs as described elsewhere herein may be used with any other patient contacting component of a patient interface device, such as, without limitation, cheek supports and chin supports, to provide better sealing properties and patient comfort.

Furthermore, while a number particular sizes, shapes, configurations and patterns of ribs have been describe herein, it should be understood that they are mean to be exemplary only and not limiting, and that the invention can have unlimited variations by varying the rib thickness, rib spacing, rib design, height of adjacent ribs, the continuous or intermittent nature of the ribs, and/or the material used for individual ribs.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A patient interface device for delivering a flow of breathing gas to an airway of a patient, comprising:
   a patient contacting component having a patient contacting surface structured to face toward a face of the patient when the patient interface device is donned by the patient, the patient contacting surface including a plurality of ribs extending therefrom, wherein one or more of the ribs extend intermittently around the patient contacting surface, wherein one or more of the ribs extend concentrically and continuously around the patient contacting surface, wherein the plurality of ribs includes a first rib, a second rib, and a third rib, wherein the second rib is adjacent to the first rib and the third rib, wherein the first rib, the second rib, and the third rib extend substantially in parallel with each other, wherein, at a selected point along a length of the second rib, the first rib and the second rib are spaced apart by a first distance and the second rib and the third rib are spaced apart by a second distance, and wherein the first distance and the second distance are different.

2. The patient interface device according to claim 1, wherein at least one of the plurality of ribs has a different length, height or thickness than at least another one of the plurality of ribs.

3. The patient interface device according to claim 1, wherein the patient contacting component is a mask comprising a cushion portion, the patient contacting surface being part of the cushion portion, and wherein the ribs extend around a cavity defined by the patient contacting surface in a concentric pattern.

4. The patient interface device according to claim 1, wherein a spacing between the ribs ranges from 0.025-0.150 mm, and a height of the ribs ranges from 0.025-0.200 mm.

5. The patient interface device according to claim 4, wherein the ribs are formed by nano etching the patient contacting surface.

6. A pressure support system, comprising:
   a pressure generating device structured to produce a flow of breathing gas; and
   a patient interface device operatively coupled to the pressure generating device and structured to deliver the flow of breathing gas to an airway of a patient, the patient interface device comprising:
   a patient contacting component, the patient contacting component having a patient contacting surface structured to face toward a face of the patient when the patient interface device is donned by the patient, the patient contacting surface including a plurality of ribs extending therefrom, wherein one or more of the ribs extend intermittently around the patient contacting surface, wherein one or more of the ribs extend concentrically and continuously around the patient contacting surface, wherein the plurality of ribs includes a first rib, a second rib, and a third rib, wherein the second rib is adjacent to the first rib and the third rib, wherein the first rib, the second rib, and the third rib extend substantially in parallel with each other, wherein, at a selected point along a length of the second rib, the first rib and the second rib are spaced apart by a first distance and the second rib and the third rib are spaced apart by a second distance, and wherein the first distance and the second distance are different.

7. The pressure support system according to claim 6, wherein at least one of the plurality of ribs has a different length, height or thickness than at least another one of the plurality of ribs.

8. The pressure support system according to claim 6, wherein the patient contacting component is a mask comprising a cushion portion, the patient contacting surface being part of the cushion portion, and wherein the ribs extend around a cavity defined by the patient contacting surface in a concentric pattern.

9. The pressure support system according to claim 6, wherein a spacing between the ribs ranges from 0.025-0.150 mm, and a height of the ribs ranges from 0.025-0.200 mm.

10. The pressure support system according to claim 9, wherein the ribs are formed by nano etching the patient contacting surface.

11. A patient interface device for delivering a flow of breathing gas to an airway of a patient, comprising:
   a patient contacting component having a patient contacting surface structured to face toward a face of the patient when the patient interface device is donned by the patient, the patient contacting surface including a plurality of ribs extending therefrom, wherein one or more of the ribs extend intermittently around the patient contacting surface, wherein one or more of the ribs extend concentrically and continuously around the patient contacting surface, wherein the plurality of ribs includes a first rib and a second rib adjacent to the first rib, wherein, at a selected point along a length of the patient contacting component, a first cross-section of the first rib has a different height than a second cross-section of the second rib, the first-cross section being adjacent to the second cross-section.

12. A pressure support system, comprising:

a pressure generating device structured to produce a flow of breathing gas; and operatively coupled to the pressure generating system and structured to deliver the flow of breathing gas to an airway of a patient, the patient interface device comprising:

a patient contacting component, the patient contacting component having a patient contacting surface structured to face toward a face of the patient when the patient interface device is donned by the patient, the patient contacting surface including a plurality of ribs extending therefrom, wherein one or more of the ribs extend intermittently around the patient contacting surface, wherein one or more of the ribs extend concentrically and continuously around the patient contacting surface, wherein the plurality of ribs includes a first rib and a second rib adjacent to the first rib, wherein, at a selected point along a length of the patient contacting component, a first cross-section of the first rib has a different height than a second cross-section of the second rib, the first-cross section being adjacent to the second cross-section.

\* \* \* \* \*